US008563769B2

(12) United States Patent
Tsugita et al.

(10) Patent No.: US 8,563,769 B2
(45) Date of Patent: Oct. 22, 2013

(54) FLUORINE-CONTAINING COMPOUND, FLUORINE-CONTAINING SURFACTANT AND COMPOSITIONS CONTAINING SAME

(75) Inventors: Katsuyuki Tsugita, Chigasaki (JP); Masato Mitsuhashi, Chigasaki (JP)

(73) Assignee: AGC Seimi Chemical Co., Ltd., Chigasaki-shi (JP)

( * ) Notice: Subject to any disclaimer, the term of this patent is extended or adjusted under 35 U.S.C. 154(b) by 137 days.

(21) Appl. No.: 13/388,195

(22) PCT Filed: Jul. 26, 2010

(86) PCT No.: PCT/JP2010/062517
§ 371 (c)(1),
(2), (4) Date: Jan. 31, 2012

(87) PCT Pub. No.: WO2011/013615
PCT Pub. Date: Feb. 3, 2011

(65) Prior Publication Data
US 2012/0132103 A1    May 31, 2012

(30) Foreign Application Priority Data

Jul. 31, 2009    (JP) ................ 2009-179070

(51) Int. Cl.
| C07C 305/04 | (2006.01) |
| C07C 309/14 | (2006.01) |
| B01F 17/00 | (2006.01) |
| B01F 17/16 | (2006.01) |
| C09G 1/04 | (2006.01) |
| C09G 1/16 | (2006.01) |
| C09K 3/00 | (2006.01) |

(52) U.S. Cl.
USPC ............... 562/107; 106/3; 516/198; 516/201; 524/165; 562/104

(58) Field of Classification Search
USPC ....... 106/3; 516/198, 201; 524/165; 562/104, 562/107
See application file for complete search history.

(56) References Cited

U.S. PATENT DOCUMENTS

| 5,571,858 A | 11/1996 | De La Poterie et al. |
| 5,648,527 A | 7/1997 | Prossel et al. |
| 5,648,528 A | 7/1997 | Prossel et al. |
| 5,672,647 A | 9/1997 | De La Poterie et al. |
| 5,852,148 A | 12/1998 | Behr et al. |
| 6,048,952 A | 4/2000 | Behr et al. |
| 2003/0153780 A1 | 8/2003 | Haniff et al. |

FOREIGN PATENT DOCUMENTS

| CN | 1535260 A | 10/2004 |
| EP | 0 526 976 A1 | 2/1993 |
| JP | 61 100266 | 5/1986 |
| JP | 5 345732 | 12/1993 |
| JP | 7 173034 | 7/1995 |
| JP | 8 48655 | 2/1996 |
| JP | 10 218854 | 8/1998 |
| JP | 11 310789 | 11/1999 |
| JP | 2002 90937 | 3/2002 |

OTHER PUBLICATIONS

Combined Office Action and Search Report issued May 10, 2013 in Chinese Patent Application No. 201080032156.8.
Robert Kaplanek, et al, "Amphiphilic perfluoroalkylated sulfones and sulfonate betaines", Journal of Fluorine Chemistry 128, 2007, pp. 789-796.
Prescher, D., "Nitrogen-containing Fluorosurfactants," Tenside Surfactants Detergents, vol. 29, No. 5, pp. 337-341, (1992).
Szonyi, S., "Synthese de Nouveaux Tensio-Actifs F-Alkyles Bifonctionnels et Application a la Preparation de Mousses Extinctrices Polyvalentes," Journal of Fluorine Chemistry, vol. 30, pp. 37-57, (1985) (with English abstract).
International Search Report Issued Aug. 17, 2010 in PCT/JP10/62517 Filed Jul. 26, 2010.

*Primary Examiner* — Anthony J Green
(74) *Attorney, Agent, or Firm* — Oblon, Spivak, McClelland, Maier & Neustadt, L.L.P.

(57) ABSTRACT

A fluorine-containing compound exhibiting excellent surface tension-reducing ability despite the absence of perfluoroalkyl group having a chain length of 8 or more which had been the cause of the PFOS and PFOA problems and use of a fluorine material with low environmental load is provided. Also provided are a fluorine-containing surfactant and a composition thereof, an aqueous resin emulsion and a floor polish composition containing such surfactant. The fluorine-containing compound is represented by the following formula (1): $Rf^1—C_pH_{2p}—CH(OH)—C_qH_{2q}—NR—C_rH_{2r}—(O)_n—SO_3M$ (1) wherein $Rf^1$ is a $C_{1-6}$ perfluoroalkyl group, p, q, and r are independently an integer of 1 to 6, M is a cationic atom or atomic group, n is 0 or 1, R is hydrogen atom, a $C_{1-12}$ alkyl group, or a group represented by the following formula (2):

$$Rf^2—C_sH_{2s}—CH(OH)—C_tH_{2t}— \quad (2)$$

wherein $Rf^2$ is a $C_{1-6}$ perfluoroalkyl group, and s and t are independently an integer of 1 to 6.

20 Claims, No Drawings

FLUORINE-CONTAINING COMPOUND, FLUORINE-CONTAINING SURFACTANT AND COMPOSITIONS CONTAINING SAME

TECHNICAL FIELD

This invention relates to a fluorine-containing compound, fluorine-containing surfactant, and compositions containing the same.

BACKGROUND ART

When a surfactant is incorporated in a composition, the surfactant gathers to the interface and reduces the surface tension, and spreadability and permeability are thereby improved.

Fluorine surfactants have been known to have a surface tension-reducing ability which is superior to that of the corresponding hydrocarbon surfactant or silicone surfactant. Accordingly, fluorine surfactants have been used in a wide variety of fields (see, for example, Patent Literatures 1 to 3).

Examples of the widely used fluorine surfactant include perfluorooctanesulfonic acid (PFOS), perfluorooctanoic acid (PFOA), and fluorine surfactants based on such surfactants. PFOS has a structure wherein a perfluoroalkyl group is directly bonded to sulfonyl group, and PFOA has a structure wherein a perfluoroalkyl group is directly bonded to carboxy group. In view of the superior performance, perfluoroalkyl groups having a chain length of 8 or more are often selected.

However, due to the extremely hard decomposition of the PFOS and PFOA and high bioaccumulativity of the PFOS and PFOA, global environmental pollution is feared for these substances. In view of the PFOS and PFOA problems, compounds having a perfluoroalkyl group with a chain length of 8 or more have become problematic, and purchase and use of the compound having a perfluoroalkyl group with a chain length of 8 or more are becoming difficult due to the regulatory compliance in various countries and voluntary restraints of companies.

One method for solving the PFOS and PFOA problems is use of a compound having a perfluoroalkyl group with a chain length of less than 8 for the fluorine surfactant. However, the perfluoroalkyl group having a chain length of 8 or more had been preferentially chosen in view of the excellence in the surface tension-reducing ability and leveling property, and the compound having the perfluoroalkyl group with shorter chain length had the problem of significantly reduced surface tension-reducing ability and leveling property.

CITATION LIST

Patent Literature

Patent Literature 1: JP 11-310789 A
Patent Literature 2: JP 2002-90937 A
Patent Literature 3: JP 07-173034 A

SUMMARY OF INVENTION

Technical Problems

The present invention provides a fluorine-containing compound which exhibits excellent surface tension-reducing ability despite the absence of the perfluoroalkyl group having a chain length of 8 or more which had been the cause of the PFOS and PFOA problems and use of a fluorine material with low environmental load. The present invention also provides a fluorine-containing surfactant and a composition containing such fluorine-containing surfactant. The present invention also provides an aqueous resin emulsion and a floor polish composition containing such fluorine-containing surfactant which exhibit high leveling property.

Solution to Problems

The present invention provides a fluorine-containing compound represented by the following formula (1):

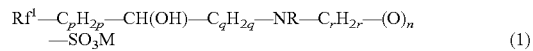

$$Rf^1-C_pH_{2p}-CH(OH)-C_qH_{2q}-NR-C_rH_{2r}-(O)_n-SO_3M \qquad (1)$$

wherein
$Rf^1$ represents a perfluoroalkyl group containing 1 to 6 carbon atoms,
p, q, and r independently represent an integer of 1 to 6,
M represents a cationic atom or atomic group,
n represents 0 or 1,
R represents hydrogen atom, an alkyl group containing 1 to 12 carbon atoms, or a group represented by the following formula (2):

$$Rf^2-C_sH_{2s}-CH(OH)-C_tH_{2t}- \qquad (2)$$

wherein
$Rf^2$ is a perfluoroalkyl group containing 1 to 6 carbon atoms, and
s and t independently represent an integer of 1 to 6.

The fluorine-containing compound is preferably the one wherein n in the formula (1) is 0.

Also, the fluorine-containing compound is preferably the one wherein $Rf^1$ in the formula (1) is a perfluoroalkyl group containing 6 carbon atoms.

Furthermore, the fluorine-containing compound is preferably the one wherein R in the formula (1) is a group represented by the formula (2), and more preferably, the one wherein $Rf^2$ is a perfluoroalkyl group containing 6 carbon atoms.

The present invention also provides a fluorine-containing surfactant comprising the compound represented by the formula (1).

The present invention also provides a surfactant composition containing the fluorine-containing surfactant and an aqueous medium.

The present invention also provides an aqueous resin emulsion containing the fluorine-containing surfactant.

The present invention also provides a floor polish composition containing the fluorine-containing surfactant.

ADVANTAGEOUS EFFECTS OF INVENTION

The present invention provides a novel fluorine-containing compound which can be used as a surfactant having a sufficiently high surface tension-reducing ability even when used at a low concentration. In addition, compositions having blended a surfactant therein are recently prepared by using an aqueous medium containing water as its main component in consideration of working convenience, safety, and environmental concern, and the surfactant of the present invention is particularly useful for use with such an aqueous medium.

The surfactant composition of the present invention containing the fluorine-containing surfactant of the present invention can be used in various applications since it has sufficiently high surface tension-reducing ability even when the surfactant concentration in use is low.

The fluorine-containing surfactant of the present invention is capable of reducing the surface tension of the aqueous resin emulsion, and hence, the surface tension of the resin emulsion of the present invention. Accordingly, the aqueous resin emulsion of the present invention has excellent leveling property, and the floor and the like treated with the fluorine-containing surfactant of the present invention has excellent outer appearance. Similarly, the floor polish composition of the present invention containing the fluorine-containing surfactant of the present invention has excellent leveling property, and capable of imparting good outer appearance with the floor.

DESCRIPTION OF EMBODIMENTS

In this specification, the compound represented by the formula (1) is also referred to as the compound (1), and this applies to the compounds and groups represented by other formulae. Unless otherwise noted, "%" means "% by mass".

In the compound (1) of the present invention, $Rf^1$ represents a perfluoroalkyl group containing 1 to 6 carbon atoms, and the perfluoroalkyl group may be either a straight chain or a branched group, and preferably a straight chain group. In view of the ease of the synthesis and good surface tension-reducing ability, $Rf^1$ is preferably a straight chain perfluoroalkyl group containing 4 to 6 carbon atoms, and among these, and more preferably, a straight chain perfluoroalkyl group containing 4 or 6 carbon atoms in view of availability of the starting materials. Most preferably, $Rf^1$ is a straight chain perfluoroalkyl group containing 6 carbon atoms in view of the good surface tension-reducing ability.

In the compound (1) of the present invention, p, q, and r are respectively an integer of 1 to 6, and the alkylene group determined by the number of carbon atoms p, q, and r may be either a straight chain or a branched group, and preferably a straight chain group. Among these, the preferred is a straight chain alkylene group containing 1 to 3 carbon atoms, and in particular, p and q are preferably 1 so that —$C_pH_{2p}$— and —$C_qH_{2q}$— are methylene, and r is preferably 1 to 2 so that —$C_rH_{2r}$— is preferably methylene or ethylene. An alkylene group with short chain length is preferable since solubility in water is improved, and inhibition of the surfactant activity is less likely to be inhibited when used with other hydrocarbon organic solvent and surfactant in a mixture.

In the compound (1) of the present invention, M is cationic atom or atomic group. Examples of such cationic atom or atomic group include hydrogen atom, alkaline metal, alkaline earth metal, or ammonium group having its hydrogen atoms partially or entirely substituted with an alkyl group or hydroxyalkyl group (the alkyl group containing 1 or 2 carbon atoms). In view of the reduced amount of by-products after the synthesis and higher solubility in the solvent, M is preferably an alkaline metal, and more preferably Na, K, or Li.

In the compound (1) of the present invention, n is 0 or 1, and n is preferably 0 in view of the thermal and alkaline stability and surface tension-reducing ability of the compound (1).

In the compound (1) of the present invention, R is hydrogen atom, an alkyl group containing 1 to 12 carbon atoms, or a group represented by the following formula (2):

$$Rf^2\text{—}C_sH_{2s}\text{—}CH(OH)\text{—}C_tH_{2t}\text{—} \qquad (2)$$

wherein definition and preferred embodiments of the $Rf^2$ are as described above for the $Rf^1$, and definition, and preferred embodiments of the s and t are as described above for the p and q.

Introduction of an alkyl group is effective to improve compatibility of the compound with other hydrocarbon organic solvent and surfactant by the interaction with therewith when the compound is used in a mixture. However, simply in view of the surface tension-reducing ability, R is preferably a group represented by the formula (2) or hydrogen atom, and in particular, a group represented by the formula (2) in view of the excellent surface tension-reducing ability when added to an aqueous resin emulsion.

Preferable examples of the compound (1) of the present invention are the compounds as described below, and the most preferred are compounds (1A-66a) to (1A-66c) wherein n is 0, R is formula (2), and $Rf^1$ and $Rf^2$ are a perfluoroalkyl group containing 6 carbon atoms

| | |
|---|---|
| $C_6F_{13}$—$CH_2CH(OH)CH_2NH(CH_2)_mSO_3Li$ | (1A-60a) |
| $C_6F_{13}$—$CH_2CH(OH)CH_2NH(CH_2)_mSO_3Na$ | (1A-60b) |
| $C_6F_{13}$—$CH_2CH(OH)CH_2NH(CH_2)_mSO_3K$ | (1A-60c) |
| $C_4F_9$—$CH_2CH(OH)CH_2NH(CH_2)_mSO_3Li$ | (1A-40a) |
| $C_4F_9$—$CH_2CH(OH)CH_2NH(CH_2)_mSO_3Na$ | (1A-40b) |
| $C_4F_9$—$CH_2CH(OH)CH_2NH(CH_2)_mSO_3K$ | (1A-40c) |
| $(C_6F_{13}$—$CH_2CH(OH)CH_2)_2N(CH_2)_mSO_3Li$ | (1A-66a) |
| $(C_6F_{13}$—$CH_2CH(OH)CH_2)_2N(CH_2)_mSO_3Na$ | (1A-66b) |
| $(C_6F_{13}$—$CH_2CH(OH)CH_2)_2N(CH_2)_mSO_3K$ | (1A-66c) |
| $(C_4F_9$—$CH_2CH(OH)CH_2)_2N(CH_2)_mSO_3Li$ | (1A-44a) |
| $(C_4F_9$—$CH_2CH(OH)CH_2)_2N(CH_2)_mSO_3Na$ | (1A-44b) |
| $(C_4F_9$—$CH_2CH(OH)CH_2)_2N(CH_2)_mSO_3K$ | (1A-44c) |
| $C_6F_{13}$—$CH_2CH(OH)CH_2(C_4F_9$—$CH_2CH(OH)CH_2)N(CH_2)_mSO_3Li$ | (1A-64a) |
| $C_6F_{13}$—$CH_2CH(OH)CH_2(C_4F_9$—$CH_2CH(OH)CH_2)N(CH_2)_mSO_3Na$ | (1A-64b) |
| $C_6F_{13}$—$CH_2CH(OH)CH_2(C_4F_9$—$CH_2CH(OH)CH_2)N(CH_2)_mSO_3K$ | (1A-64c) |
| $C_6F_{13}$—$CH_2CH(OH)CH_2NH(CH_2)_mOSO_3Li$ | (1B-60a) |
| $C_6F_{13}$—$CH_2CH(OH)CH_2NH(CH_2)_mOSO_3Na$ | (1B-60b) |
| $C_6F_{13}$—$CH_2CH(OH)CH_2NH(CH_2)_mOSO_3K$ | (1B-60c) |
| $C_4F_9$—$CH_2CH(OH)CH_2NH(CH_2)_mOSO_3Li$ | (1B-40a) |
| $C_4F_9$—$CH_2CH(OH)CH_2NH(CH_2)_mOSO_3Na$ | (1B-40b) |
| $C_4F_9$—$CH_2CH(OH)CH_2NH(CH_2)_mOSO_3K$ | (1B-40c) |
| $(C_6F_{13}$—$CH_2CH(OH)CH_2)_2N(CH_2)_mOSO_3Li$ | (1B-66a) |
| $(C_6F_{13}$—$CH_2CH(OH)CH_2)_2N(CH_2)_mOSO_3Na$ | (1B-66b) |
| $(C_6F_{13}$—$CH_2CH(OH)CH_2)_2N(CH_2)_mOSO_3K$ | (1B-66c) |
| $(C_4F_9$—$CH_2CH(OH)CH_2)_2N(CH_2)_mOSO_3Li$ | (1B-44a) |
| $(C_4F_9$—$CH_2CH(OH)CH_2)_2N(CH_2)_mOSO_3Na$ | (1B-44b) |
| $(C_4F_9$—$CH_2CH(OH)CH_2)_2N(CH_2)_mOSO_3K$ | (1B-44c) |
| $C_6F_{13}$—$CH_2CH(OH)CH_2(C_4F_9$—$CH_2CH(OH)CH_2)N(CH_2)_mOSO_3Li$ | (1B-64a) |
| $C_6F_{13}$—$CH_2CH(OH)CH_2(C_4F_9$—$CH_2CH(OH)CH_2)N(CH_2)_mOSO_3Na$ | (1B-64b) |

$$C_6F_{13}\text{—}CH_2CH(OH)CH_2(C_4F_9\text{—}CH_2CH(OH)CH_2)$$
$$N(CH_2)_mOSO_3K \quad (1B\text{-}64c)$$

wherein m is an integer of 1 to 3.

The compound (1) of the present invention is not particularly limited for its production method, and it may be produced by using a reaction and equipment known in organic chemistry selected depending on the intended purpose.

In an exemplary production method of the compound (1) of the present invention, when n is 0 and q is 1, an Rf epoxide (3) having a perfluoroalkyl group containing 1 to 6 carbon atoms is reacted with aminosulfonic acid (4) under a basic condition.

[Chemical Formula 1]

(3)

$$NHR\text{—}C_rH_{2r}\text{—}SO_3M \quad (4)$$

(wherein symbols are as defined above)

The Rf epoxide (3) used may comprise either one Rf epoxide (3) or a mixture of two or more Rf epoxides (3). The Rf epoxide (3) may be a commercially available product, for example, the one from Daikin Chemical Sales Company. Preferable examples of the aminosulfonic acid (4) are taurine, aminomethanesulfonic acid, 3-aminopropanesulfonic acid, and N-methyltaurine in view of availability. Exemplary commercially available aminosulfonic acids (4) include those from Wako Pure Chemical Industries, Ltd., Tokyo Kasei Kogyo Co. Ltd., Sigma-Aldrich Japan, and Honjo Chemical Corporation. When R in the aminosulfonic acid (4) is H and, 2 fold or more of the Rf epoxide (3) is used in relation to 1 mole of the aminosulfonic acid (4), major part of the resulting compound (1) will be a structure wherein R is a group represented by the formula (2).

In an exemplary production method of the compound (1) of the present invention, when n is 1 and q is 1, the Rf epoxide (3) having a perfluoroalkyl group containing 1 to 6 carbon atoms is reacted with an aminosulfuric acid ester (5):

$$NHR\text{—}C_rH_{2r}\text{—}O\text{—}SO_3M \quad (5)$$

(wherein symbols are as defined above)
under a basic condition. The Rf epoxide (3) used may comprise either one Rf epoxide (3) or a mixture of two or more Rf epoxides (3). Preferable examples of the aminosulfuric acid ester (5) are 2-aminoethyl hydrogen sulfate in view of the availability. Exemplary commercially available aminosulfuric acid esters (5) include those from Wako Pure Chemical Industries, Ltd. and Tokyo Kasei Kogyo Co. Ltd.

When R in the aminosulfonic acid ester (5) is H, and 2 fold or more of the Rf epoxide (3) is used in relation to 1 mole of the aminosulfuric acid ester (5), major part of the resulting compound (1) will be a structure wherein R is a group represented by the formula (2).

The reaction solvent is not particularly limited. However, in consideration of the solubility, workability, and cost, preferred is the use of water or an alcohol solvent, and in particular, water, methanol, ethanol, propyl alcohol, or a mixture thereof.

The reaction temperature is not particularly limited. However, the reaction is preferably conducted at a temperature of 0° C. to 150° C., and more preferably at 50° C. to 100° C. since use of an excessively low temperature invites low reaction speed while excessively high temperature results in the generation ob by-products. The pressure is also not particularly limited while the reaction is preferably conducted at a pressure of atmospheric pressure to 1 MPa, and more preferably at atmospheric pressure in view of the handling convenience.

As described above, the reaction is conducted under basic condition. The base used is not particularly limited, and exemplary preferable bases include alkaline metal hydroxides such as potassium hydroxide, sodium hydroxide, and lithium hydroxide. While the M in the compound (1) of the present invention may be introduced by substitution after the synthesis, use of an alkaline metal hydroxide as described above that would enable use of the atoms in the base is preferable for reducing number of production steps.

The fluorine-containing surfactant of the present invention may comprise either one compound (1) or a mixture of two or more compounds (1). Exemplary mixtures include a combination of those having different perfluoroalkyl group chain lengths and a combination of the one wherein R is hydrogen atom and the one wherein R is a group represented by the formula (2).

The surfactant composition of the present invention may solely comprise the fluorine-containing surfactant of the present invention and an aqueous medium. However, the surfactant composition may further contain other surfactants, and exemplary other surfactants include fluorine, silicone, and hydrocarbon surfactants, which may be incorporated at a ratio adequately determined by the intended use.

The surfactant composition of the present invention may contain either one compound (1) or a mixture of two or more compounds (1).

Examples of the aqueous medium used in the surfactant composition of the present invention include water, a water-soluble organic solvent, and a mixture of water and a water-soluble organic solvent. Exemplary water-soluble organic solvents include alcohols such as methanol, ethanol, isopropyl alcohol, and tertiary butyl alcohol; ketones such as acetone, methyl ethyl ketone, and methyl isobutyl ketone; esters such as methyl acetate and ethyl acetate; aprotic polar solvents such as N,N-dimethylformamide, dimethylsulfoxide, sulfolane, and N-methylpyrrolidone; glycol ethers such as diethylene glycol monomethyl ether, propylene glycol monomethyl ether acetate; glycols such as ethyleneglycol and propylene glycol; and ethers such as tetrahydrofuran and dioxane.

Concentration of the fluorine-containing surfactant of the present invention in the surfactant composition of the present invention is not particularly limited. However, the concentration is preferably 10 to 70%, and more preferably 15 to 60%.

When the concentration is within such range, addition of an adequate amount can be readily accomplished, and transportation cost per unit weight of the fluorine-containing surfactant will be reduced due to the reduced content of the solvent in the surfactant composition of the present invention.

In addition, when the concentration is within such range, the composition will enjoy handling convenience since viscosity will not be too high, and precipitation during the storage will also be avoided.

By adding to various liquid, the fluorine-containing surfactant and the surfactant composition of the present invention can reduce surface tension of the liquid irrespective of the composition of the solvent used in the liquid. While the amount added should be adequately determined depending on the intended use and conditions of use, content of the compound (1) is preferably in the range of 0.0001 to 5% in the conditions of actual use. The content of the compound (1) is more preferably 0.001 to 1%. When used at the content in such range, surface tension-reducing ability will be fully exerted without adversely affecting the functional properties of the main component. When the composition contains two or more types of compounds (1), total amount is preferably within the above-specified range. By the surface tension-reducing ability, the fluorine-containing surfactant and the surfactant composition of the present invention is capable of imparting functions such as leveling property, permeability, foaming property, detergent property, and emulsifying property to the liquid to which they are added.

The surfactant composition of the present invention is capable of exerting sufficient surface tension-reducing ability even at a low concentration, and therefore, it is well adapted for use in various applications. The surfactant composition of the present invention fulfills its function in a leveling agent such as wax, a foaming aid, additives of foam fire extinguisher for stable foam formation and fire extinguishing improvement, a detergent, a mold release agent, an emulsifier, an anticorrosive, a latex stabilizer, an anti-fogging agent for agricultural films, a pigment dispersant, an anti-fogging agent for agricultural films, an anti-fouling agent, a flotation concentrator, a lubricating agent, and a de-inking agent; in improving wettability and permeability of an ink, a paint, and a resist; and in imparting water- and oil-repellency to a curable resin, and it can be used for a wide variety of applications including washing and gravure printing.

The aqueous resin emulsion of the present invention may preferably contain the compound (1) at a content of up to 0.1%, more preferably at 0.001 to 0.05%, and most preferably at 0.003 to 0.05%. When the content is 0.001% or more, leveling property is easily realized, and the content of up to 0.1% is less likely to invite adverse effects on other component.

The resin used in the aqueous resin emulsion of the present invention is not particularly limited as long as it is a resin commonly used in an aqueous resin emulsion. Examples include (meth) acryl, styrene, and urethane resins, which may be a single polymer or a copolymer of a combination of resins such as acryl-styrene copolymer.

Examples of the commercially available resin emulsion include DURAPLUS 2, PRIMAL E-2409, PRIMAL B-924, DURAPLUS 3L0, PRIMAL JP-308 (all manufactured by Rohm and Haas), AE-610H, AE-945H, and AE-981H (all manufactured by JSR).

The resin used may be an alkali soluble resin.

Examples of the alkali soluble resin include PRIMAL B-644 and PRIMAL 1531B (both manufactured by Rohm and Haas).

The floor polish composition of the present invention is a composition containing the fluorine-containing surfactant of the present invention as described above.

The floor polish composition of the present invention preferably contains acrylic resin, styrene resin, urethane resin, or a combination of such resin, for example, acryl-styrene resin as the resin component. More preferably, the floor polish composition of the present invention contains such resin and an alkali-soluble resin as the resin component, and in addition, a polyolefin wax.

Exemplary polyolefin waxes include Hi-tech E-4B and Hi-tech E-8000 (both manufactured by Toho Chemical Industries Co., Ltd.).

The floor polish composition of the present invention may also be the one prepared by adding the fluorine-containing surfactant of the present invention to the commercially available resin emulsion.

In the following description, the resins including the acrylic resin and the like and the alkali-soluble resin and the polyolefin wax are together referred to as "component (P)" for the sake of convenience.

Content of the component (P) in the floor polish composition of the present invention (100%) is preferably 5 to 40%, and more preferably 10 to 35%. When the content of the component (P) is 5% or higher, functions required for a floor polish composition such as water resistance and glossiness can be readily realized. Coating on the floor can be readily conducted when the content of the component (P) is up to 40%.

It is to be noted that the content of the component (P) is the content of the solid content.

The floor polish composition of the present invention may also contain a plasticizer, a leveling aid, an antiseptic, an antifoaming agent.

Exemplary plasticizers include dibutyl phthalate, dioctyl phthalate, tributyl citrate, tributyl acetylcitrate, 2,2,4-tributyl, 1,3-pentanediol monoisobutylate, 2,2,4-trimethyl-1,3-pentanediol diisobutylate, and 2,2,4-trimethyl-1,3-pentanediol monoisobutylate, and the preferred are those other than phthalate plasticizers.

Exemplary leveling agents include tributoxyethyl phosphate.

Exemplary antiseptics include KATHON CG (manufactured by Rohm and Haas).

Exemplary antifoaming agents include FS-ANTIFOAM 013A, FS-ANTIFOAM 1277 (both manufactured by Dow Corning Toray Co., Ltd.) SE-21 and SE-39 (both manufactured by Wacker Asahikasei Silicone Co., Ltd.).

The floor polish composition of the present invention may also contain other additives such as UV absorbent, colorant, aromatic, miticide, and pH adjusting agent.

For the improvement of the leveling property, the floor polish composition of the present invention preferably contains up to 0.1%, preferably 0.001 to 0.05%, and most preferably 0.003 to 0.05% of the compound (1). When the content is 0.001% or more, the leveling property is easily realized, and the content of up to 0.1% is less likely to invite adverse effects on other component.

EXAMPLES

Next, the present invention is described in further detail by referring to the Examples which by no means limit the scope of the present invention. The structure of the compounds of the Examples are shown in Table 1.

TABLE 1

| Compound | Structure |
|---|---|
| Compound (1-1) | $CF_3(CF_2)_5CH_2CHCH_2\text{—}N(H)\text{—}CH_2CH_2SO_3Na$, with OH on the CH |
| Compound (1-2) | $CF_3(CF_2)_5CH_2CHCH_2\text{—}N(H)\text{—}CH_2CH_2SO_3K$, with OH on the CH |

TABLE 1-continued

| Compound | Structure |
|---|---|
| Compound (1-3) | $CF_3(CF_2)_5CH_2\underset{\underset{OH}{\|}}{C}HCH_2$—N(—$CH_2CH_2SO_3Na$)—$CH_2\underset{\underset{OH}{\|}}{C}HCH_2(CF_2)_5CF_3$ |
| Compound (1-4) | $CF_3(CF_2)_5CH_2\underset{\underset{OH}{\|}}{C}HCH_2$—N(—$CH_2CH_2OSO_3Na$)—$CH_2\underset{\underset{OH}{\|}}{C}HCH_2(CF_2)_5CF_3$ |
| Compound (1-5) | $CF_3(CF_2)_5CH_2\underset{\underset{OH}{\|}}{C}HCH_2$—N(—$CH_2CH_2CH_2SO_3Na$)—$CH_2\underset{\underset{OH}{\|}}{C}HCH_2(CF_2)_5CF_3$ |
| Compound (1-6) | $CF_3(CF_2)_5CH_2\underset{\underset{OH}{\|}}{C}HCH_2$—N(—$CH_2CH_2SO_3Li$)—$CH_2\underset{\underset{OH}{\|}}{C}HCH_2(CF_2)_5CF_3$ |
| Compound (1-7) | $CF_3(CF_2)_5CH_2\underset{\underset{OH}{\|}}{C}HCH_2$—N(—$CH_2CH_2CH_2SO_3Li$)—$CH_2\underset{\underset{OH}{\|}}{C}HCH_2(CF_2)_5CF_3$ |
| Compound (3-1) | $CF_3(CF_2)_5CH_2$—$CH_2$—$\underset{O}{\overset{CH_2}{\diagdown\!\diagup}}$ |

Example 1

Synthesis of Compound (1-1)

100 ml glass flask was charged with 1.5 g of sodium hydroxide, 24 g of ion exchanged water, 12 g of methanol, 12 g of isopropyl alcohol, and 5.0 g (0.04 mol) of taurine (manufactured by Wako Pure Chemical Industries, Ltd.), and the mixture was heated to 65° C. To this mixture, 15.0 g (0.04 mol) of the compound (3-1) which had been synthesized by the method known in the art was added dropwise for 2 hours, and the mixture was allowed to react at the same temperature for 21 hours to obtain a water/methanol/isopropyl alcohol solution containing 30% of the reaction product mainly comprising the compound (1-1). The reaction solution was analyzed by gas chromatography, and conversion rate of the compound (3-1) was no less than 99%.

To confirm the identity of the reaction product, a portion of the reaction solution was dried at 120° C. for 2 hours, and the resulting solid was analyzed by NMR. $^1$H-NMR and $^{13}$C-NMR spectrum data for the compound (1-1) were as shown below.

$^1$H-NMR (300 MHz, solvent: CD$_3$OD, standard substance: hexamethyldisiloxane), σ (ppm): 2.05 to 2.45 (2H), 2.50 to 2.64 (2H), 2.86 to 3.06 (6H), 4.10 (1H)

$^{13}$C-NMR (300 MHz, solvent: CD$_3$OD, standard substance: hexamethyldisiloxane), σ (ppm): 37.1 (t), 46.0, 51.5, 56.2, 64.7

The gas chromatographic analysis and the NMR spectrum data indicated substantial absence of the non-reacted compound (3-1), namely, that most of the compound (3-1) had been converted to the intended product.

Example 2

Synthesis of Compound (1-2)

100 ml glass container was charged with 2.2 g of 20% aqueous solution of potassium hydroxide, 4.8 g of ion exchanged water, 2.4 g of methanol, 2.4 g of isopropyl alcohol, 1.0 g (0.008 mol) of taurine (manufactured by Honjo Chemical Corporation), and 3.0 g (0.008 mol) of the compound (3-1) which had been synthesized by the method known in the art, and after sealing, the mixture was set on a water bath shaker to allow for the reaction to proceed at 65° C. for 15 hours to obtain a water/methanol/isopropyl alcohol solution containing 26% of the reaction product mainly comprising the compound (1-2). The reaction solution was analyzed by gas chromatography, and conversion rate of the compound (3-1) was no less than 99%.

To confirm the identity of the reaction product, a portion of the reaction solution was dried at 120° C. for 2 hours, and the resulting solid was analyzed by NMR. $^1$H-NMR and $^{13}$C-NMR spectrum data for the compound (1-2) were as shown below.

$^1$H-NMR (300 MHz, solvent: CD$_3$OD, standard substance: hexamethyldisiloxane), σ (ppm): 2.05 to 2.45 (2H), 2.50 to 2.64 (2H), 2.86 to 3.06 (6H), 4.10 (1H)

$^{13}$C-NMR (300 MHz, solvent: CD$_3$OD, standard substance: hexamethyldisiloxane), σ (ppm): 37.1 (t), 46.0, 51.5, 56.2, 64.6

The gas chromatographic analysis and the NMR spectrum data indicated substantial absence of the non-reacted compound (3-1), namely, that most of the compound (3-1) had been converted to the intended product.

Example 3

Synthesis of Compound (1-3)

3.00 ml flask was charged with 3.2 g of sodium hydroxide, 56.8 g of ion exchanged water, 30 g of methanol, 30 g of isopropyl alcohol, 10.0 g (0.08 mol) of taurine (manufactured by Wako Pure Chemical Industries, Ltd.), and 60.1 g (0.16 mol) of the compound (3-1) which had been synthesized by the method known in the art, and the mixture was allowed to react at 60° C. for 48 hours to produce a water/methanol/isopropyl alcohol solution containing 36% of the reaction product mainly comprising the compound (1-3). The reaction solution was analyzed by gas chromatography, and conversion rate of the compound (3-1) was no less than 97%.

To confirm the identity of the reaction product, a portion of the reaction solution was dried at 120° C. for 2 hours, and the resulting solid was analyzed by NMR. $^1$H-NMR and $^{13}$C-NMR spectrum data for the compound (1-3) were as shown below.

$^1$H-NMR (300 MHz, solvent: CD$_3$OD, standard substance: hexamethyldisiloxane), σ (ppm): 2.1 to 2.5 (4H), 2.5 to 2.7 (4H), 2.8 to 3.3 (6H), 4.1 (2H)

$^{13}$C-NMR (300 MHz, solvent: CD$_3$OD, standard substance: hexamethyldisiloxane), σ (ppm): 36.4 (t), 36.6 (t), 51, 6, 52.2, 62.2, 63.0, 63.6, 64.7

The gas chromatographic analysis and the NMR spectrum data indicated substantial absence of the non-reacted compound (3-1), namely, that most of the compound (3-1) had been converted to the intended product.

Example 4

Synthesis of Compound (1-4)

100 ml glass container was charged with 1.7 g of 20% aqueous sodium hydroxide, 4.6 g of ion exchanged water, 6 g of isopropyl alcohol, 1.0 g (0.007 mol) of 2-aminoethyl hydrogen sulfate (Manufactured by Tokyo Kasei Kogyo Co. Ltd.), and 5.3 g (0.014 mol) of the compound (3-1) which had been synthesized by the method known in the art, and after sealing, the mixture was set on a water bath shaker to allow for the reaction to proceed at 65° C. for 15 hours to obtain a compound reaction product mainly comprising the compound (1-4). Since solid precipitation and sedimentation of a transparent liquid was partly observed, upper layer was collected and filtered through a 0.45 μm filter to obtain a water/isopropyl alcohol solution containing 28% of the reaction product mainly comprising the compound (1-4). The yield was 78%. In the gas chromatographic analysis of the reaction solution, the conversion rate of the compound (3-1) was 96%.

To confirm the identity of the reaction product, a portion of the reaction solution was dried at 40° C. for 4 hours at a reduced pressure of 10 mmHg, and the resulting solid was analyzed by NMR. $^1$H-NMR and $^{13}$C-NMR spectrum data for the compound (1-4) were as shown below.

$^1$H-NMR (300 MHz, solvent: CD$_3$OD, standard substance: hexamethyldisiloxane), σ (ppm): 2.0 to 2.5 (4H), 2.5 to. 2.7 (4H), 2.7 to 3.0 (2H), 4.0 to 4.3 (6H)

$^{13}$C-NMR (300 MHz, solvent: CD$_3$OD, standard substance: hexamethyldisiloxane), σ (ppm): 36.6 (t), 36.8 (t), 55.1, 55.5, 63.4, 64.0, 64.8, 66.9

Example 5

Synthesis of Compound (1-5)

100 ml glass container was charged with 0.80 g of sodium hydroxide, 18.2 g of ion exchanged water, 18.2 g of isopropyl alcohol, and 2.87 g (0.02 mol) of 3-aminopropanesulfonic acid (manufactured by Sigma-Aldrich Japan), and the mixture was heated to the reflux temperature. To this mixture, 15.33 g (0.04 mol) of the compound (3-1) was added dropwise for 2.5 hours, and the reaction was allowed to proceed for 36 hours to obtain a water/isopropyl alcohol solution containing 32.7% of the reaction product mainly comprising the compound (1-5). The reaction solution was analyzed by gas chromatography, and conversion rate of the compound (3-1) was 99.6%.

To confirm the identity of the reaction product, a portion of the reaction solution was dried at 110° C. for 2 hours, and the resulting solid was analyzed by NMR. $^1$H-NMR and $^{13}$C-NMR spectrum data for the compound (1-5) were as shown below.

$^1$H-NMR (300 MHz, solvent: CD$_3$OD standard substance: hexamethyldisiloxane) σ (ppm): 1.8 to 1.9 (2H), 2.0 to 2.4 (2H), 2.4 to 2.8 (10H), 4.0 to 4.1 (2H)

$^{13}$C-NMR (300 MHz, solvent: CD$_3$OD standard substance: hexamethyldisiloxane) σ (ppm): 23.2, 36.4 to 37.0 (t), 50.3, 55.4, 55.7, 62.1, 63.0, 63.8, 64.8

The gas chromatographic analysis and the NMR spectrum data indicated substantial absence of the non-reacted compound (3-1), namely, that most of the compound (3-1) had been converted to the intended product.

Example 6

Synthesis of Compound 1-6

100 ml glass flask was charged with 1.26 g of lithium hydroxide monohydrate (manufactured by Wako Pure Chemical Industries, Ltd.), 26.75 g of ion exchanged water, 26.75 g of isopropyl alcohol, and 3.75 g (0.03 mol) of taurine (manufactured by Wako Pure Chemical Industries, Ltd.), and the mixture was heated to 78° C. To this mixture, 23.00 g (0.06 mol) of the compound (3-1) was added dropwise for 2 hours, and the reaction was allowed to proceed for 54 hours to obtain a water/isopropyl alcohol solution containing 33.0% of the reaction product mainly comprising the compound (1-6). The reaction solution was analyzed by gas chromatography, and conversion rate of the compound (3-1) was 99.5%.

To confirm the identity of the reaction product, a portion of the reaction solution was dried at 110° C. for 2 hours, and the resulting solid was analyzed by NMR. $^1$H-NMR and $^{13}$C-NMR spectrum data for the compound (1-6) were as shown below.

$^1$H-NMR (300 MHz, solvent: CD$_3$OD, standard substance: hexamethyldisiloxane), σ (ppm): 2.1 to 2.5 (4H), 2.5 to 2.7 (4H), 2.8 to 3.3 (6H), 4.1 (2H)

$^{13}$C-NMR (300 MHz, solvent: CD$_3$OD, standard substance: hexamethyldisiloxane), σ (ppm): 36.4 (t), 36.6 (t), 51, 6, 52.2, 62.2, 63.0, 63.6, 64.7

The gas chromatographic analysis and the NMR spectrum data indicated substantial absence of the non-reacted compound (3-1), namely, that most of the compound (3-1) had been converted to the intended product.

Example 7

Synthesis of Compounds 1-7

100 ml glass flask was charged with 0.84 g of lithium hydroxide monohydrate (manufactured by Wako Pure Chemical Industries, Ltd.), 18.21 g of ion exchanged water, 18.21 g of isopropyl alcohol, and 2.87 g (0.02 mol) of 3-aminopropanesulfonic acid (Sigma-Aldrich Japan), and the mixture was heated to 78° C. To this mixture, 15.34 g (0.04 mol) of the compound (3-1) was added dropwise for 2 hours, and the reaction was allowed to proceed for 24 hours to obtain a water/isopropyl alcohol solution containing 33.7% of the reaction product mainly comprising the compound (1-7). The reaction solution was analyzed by gas chromatography, and conversion rate of the compound (3-1) was 99.1%.

To confirm the identity of the reaction product, a portion of the reaction solution was dried at 110° C. for 2 hours, and the resulting solid was analyzed by NMR. $^1$H-NMR and $^{13}$C-NMR spectrum data for the compound (1-7) were as shown below.

$^1$H-NMR (300 MHz, solvent: CD$_3$OD, standard substance: hexamethyldisiloxane), σ (ppm): 1.8 to 1.9 (2H), 2.0 to 2.4 (2H), 2.4 to 2.8 (10H), 4.0 to 4.1 (2H)

$^{13}$C-NMR (300 MHz, solvent: CD$_3$OD standard substance: hexamethyldisiloxane) σ (ppm): 23.2, 36.4 to 37.0 (t), 50.3, 55.4, 55.7, 62.1, 63.0, 63.8, 64.8

The gas chromatographic analysis and the NMR spectrum data indicated substantial absence of the non-reacted compound (3-1), namely, that most of the compound (3-1) had been converted to the intended product.

Evaluation

The compounds (1-1) to (1-7) prepared in the Example 1 to 7 were respectively dissolved in water so that concentration of the solid content was at the predetermined concentration (%). The resulting aqueous solution was evaluated for static surface tension at 25° C. using an automatic surface tension meter CBVP-A3 (manufactured by Kyowa Interface Science) by Wilhelmy method. The evaluation results of are shown in 2.

The dilution with water was conducted based on the concentration of the solid content which was determined by drying the reaction solution obtained in each Example at 120° C. for 2 hours to measure the weight (g) of the remaining dried content after the removal of the solvent.

Comparative Example 1

A fluorine surfactant "Forafac 1157" (concentration of the solid content, 25%) commercially available from Du Pont was diluted with water to a predetermined concentration, and evaluated by repeating the procedure of the Examples.

According to JP 07-173034 A, Forafac 1157 has the following chemical structure:

$$C_6F_{13}\text{—}C_2H_4\text{—}SO_2NH(CH_2)_3\text{—}N^+(CH_3)_2\text{—}CH_2COO^-.$$

However, Forafac 1157 is described in the JP 07-173034 A as Forafac 1157 from Atochem.

Comparative Example 2

As an example of the commercially available fluorine surfactant containing 6 carbon atoms, value of the surface tension at 25° C. described in the catalog of an anionic surfactant "Capstone FS-10" (perfluoroalkylsulfonic acid) from Du Pont is shown in Table 2.

TABLE 2

| Surface tension of the aqueous solution (mN/m) | | |
|---|---|---|
| | Solid content | |
| | 0.1% | 0.01% |
| Example 1 (Compound (1-1)) | 14.4 | 16.2 |
| Example 2 (Compound (1-2)) | 14.6 | 16.5 |
| Example 3 (Compound (1-3)) | 14.9 | 20.4 |
| Example 4 (Compound (1-4)) | 16.2 | 19.6 |
| Example 5 (Compound (1-5)) | 15.3 | 17.6 |
| Example 6 (Compound (1-6)) | 14.6 | 18.9 |
| Example 7 (Compound (1-7)) | 15.1 | 16.8 |
| Comparative Example 1 | 16.1 | 26.0 |
| Comparative Example 2 | 23.5 | 48.5 |

As evident from Table 2, decrease in the surface tension-reducing ability with the decrease in the concentration of the compound was not so evident in the case of the compounds (1-1) to (1-7) of the present invention. The surface tension-reducing ability was particularly-remarkable at the low concentration of 0.01% compared to the betaine compound having a chain length of 6 which is generally conceived to have a high surface tension-reducing ability, which was the compound of the Comparative Example 1.

The surface tension-reducing ability was also superior to the commercially available perfluoroalkylsulfonic acid having a chain length of 6, which was the compound of the Comparative Example 2.

Next, aqueous resin emulsions and floor polish compositions were prepared by using the compounds of the present invention or comparative compounds as described below to evaluate the performance.

The comparative compounds were synthesized by a method known in the art from commercially available starting materials.

Rf—COONH$_4$         Comparative Compound 3:

(wherein Rf is a straight chain perfluoroalkyl group containing on average 9 carbon atoms)

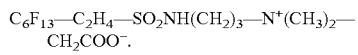
COONa        Comparative Compound 4:

$C_4F_9$—SO$_3$Na        Comparative Compound 5:

Example 8

Aqueous Resin Emulsion

A styrene-butadiene based resin emulsion 0569 (manufactured by JSR Corporation) was diluted 5 fold with water, and aqueous solution of the compound of the present invention which had been preliminarily adjusted to 1% was added to prepare an aqueous resin emulsion so that the amount of the compound was 0.012% of the total emulsion.

The thus prepared aqueous resin emulsions were evaluated for their static surface tension by repeating the procedure of the [Evaluation]. The results are shown in 3.

The blank is 5 fold dilution of the resin emulsion before the addition of the compound.

Comparative Example 3

The procedure of Example 8 was repeated except that the compound of the present invention was replaced with the comparative compound shown in Table 3 to prepare an aqueous resin emulsion and conduct the evaluation. The results are shown in Table 3.

TABLE 3

| Surface tension of the aqueous resin emulsion composition (mN/m) | | | | | | | |
|---|---|---|---|---|---|---|---|
| Compound added | | | | | | | |
| Compound of the present invention | | | | | Comparative Compound | | |
| 1-1 | 1-3 | 1-5 | 1-6 | 1-7 | 3 | 4 | Blank |
| Surface tension 25.3 | 16.8 | 17.2 | 19.0 | 17.9 | 30.6 | 32.0 | 44.8 |

Example 9

Floor Polish Composition

The components shown in Table 4 were mixed to prepare a floor polish composition. An aqueous solution of each of the compounds (1-1) to (1-7) was preliminarily prepared, and an amount corresponding to the content shown in Table 4 was mixed to prepare Composition Examples 1 to 10. In Table 4, amount of the components are indicated by "parts by weight".

Comparative Example 4

The procedure of Example 9 was repeated except that the compounds (1-1) to (1-7) were replaced with the comparative compounds 3 to 5 to prepare floor polish compositions. These floor polish compositions were designated Comparative Composition Examples 1 to 5.

The resulting floor polish compositions were evaluated for their leveling property by the procedure as described below. The results are shown in 4.

Evaluation Leveling Property

Leveling property was evaluated according to JIS K-3920. The tool used was a paint brush, and a homogeneous vinyl floor tile (product name "MS-5608" manufactured by TOLI Corporation) was used for the floor tile. The evaluation was conducted under the conditions of 5° C. and a humidity of 60%. The performance was evaluated by the following criteria. The floor polish composition exhibiting good leveling property also exhibited excellent smoothness and the coated floor tile had excellent outer appearance.

A: no coating streak or irregularity
B: either one or both of slight coating streak and slight coating irregularity
C: either one or both of clear coating streak and clear slight coating irregularity.
D: significant difference in the outer appearance compared to the blank but with marked coating streak and marked coating irregularity
E: outer appearance equivalent to the blank "Blank" is the composition not containing the compound of the present invention or the comparative compound. Blank 1 is the blank corresponding to the Composition Examples 1 to 8 and the Comparative Composition Examples 1 to 5, and the blank 2 is the blank corresponding to the Composition Examples 9 and 10.

The components in the Table 4 other than the compounds of the present invention and comparative compounds are as described below.

<Aqueous Medium>
Aqueous medium 1: water.
Aqueous medium 2: diethylene glycol monoethyl ether (manufactured by Wako Pure Chemical Industries, Ltd.)
Aqueous medium 3: dipropylene glycol monomethyl ether (manufactured by Wako Pure Chemical Industries, Ltd.)

<Resin>
Resin 1: PRIMAL 1531B (product name, an acrylic resin emulsion having a solid content of 38% by weight manufactured by Rohm and Haas)
Resin 2: DURAPLUS 2 (product name, an acrylic resin emulsion having a solid content of 38% by weight manufactured by Rohm and Haas)
Resin 3: PRIMAL JP-308 (product name, an acrylic resin emulsion having a solid content of 39% by weight manufactured by Rohm and Haas)

<Other Components>
Wax: Hi-tech E-4000 (product name, a polyethylene wax having a solid content of 40% by weight manufactured by Toho Chemical Industries Co., Ltd.)
Plasticizer: TEXANOL (product name, 2,2,4-trimethyl-1,3-pentanediol monoisobutylate, manufactured by Eastman Chemical)
Aid (leveling aid): tributoxyethyl phosphate (manufacture by Daihachi Chemical Industry Co., Ltd.)

As evident from Tables 3 and 4, when the compound of the present invention is added to an aqueous resin emulsion, the compound exhibits higher surface tension-reducing ability, which is the property required for developing the wettability and leveling property, compared to the comparative compound 3 which is the compound commonly used in the art and the comparative compound 4 having the structure similar to the compound of the present invention. Accordingly, in the

TABLE 4

| | Composition Examples | | | | | | | | | | Comparative Composition Examples | | | | | Blank | |
|---|---|---|---|---|---|---|---|---|---|---|---|---|---|---|---|---|---|
| | 1 | 2 | 3 | 4 | 5 | 6 | 7 | 8 | 9 | 10 | 1 | 2 | 3 | 4 | 5 | 1 | 2 |
| Compound (1-3) | 0.015 | — | — | — | 0.009 | — | 0.0045 | — | 0.014 | — | — | — | — | — | — | — | — |
| Compound (1-5) | — | 0.015 | — | — | — | 0.009 | — | 0.0045 | — | 0.014 | — | — | — | — | — | — | — |
| Compound (1-6) | — | — | 0.015 | — | — | — | — | — | — | — | — | — | — | — | — | — | — |
| Compound (1-7) | — | — | — | 0.015 | — | — | — | — | — | — | — | — | — | — | — | — | — |
| Comparative Compound 3 | — | — | — | — | — | — | — | — | — | — | 0.015 | 0.009 | 0.0045 | — | — | — | — |
| Comparative Compound 4 | — | — | — | — | — | — | — | — | — | — | — | — | — | 0.015 | — | — | — |
| Comparative Compound 5 | — | — | — | — | — | — | — | — | — | — | — | — | — | — | 0.015 | — | — |
| Aqueous medium 1 | 43.51 | | | | | | | | 39.08 | | 43.51 | | | | | 43.51 | 39.08 |
| Aqueous medium 2 | 3.64 | | | | | | | | 7.5 | | 3.64 | | | | | 3.64 | 7.5 |
| Aqueous medium 3 | 1.73 | | | | | | | | 1.74 | | 1.73 | | | | | 1.73 | 1.74 |
| Aqueous resin 1 | 2.39 | | | | | | | | 2.7 | | 2.39 | | | | | 2.39 | 2.7 |
| Aqueous resin 2 | 38.36 | | | | | | | | — | | 38.36 | | | | | 38.36 | — |
| Aqueous resin 3 | — | | | | | | | | 38.67 | | — | | | | | — | 38.67 |
| Wax | 6.84 | | | | | | | | 7.07 | | 6.84 | | | | | 6.84 | 7.07 |
| Plasticizer | 0.84 | | | | | | | | — | | 0.84 | | | | | 0.84 | — |
| Aid | 1.17 | | | | | | | | 1.79 | | 1.17 | | | | | 1.17 | 1.79 |
| Evaluation of leveling property | A | A | A | A | A | A | B | B | A | A | A | B | C | C | E | E | E | actual use, the compound of the present invention will exert its function at the equivalent or lower concentration.

The invention claimed is:

1. A fluorine-comprising compound of formula (1):

$$Rf^1-C_pH_{2p}-CH(OH)-C_qH_{2q}-NR-C_rH_{2r}-(O)_n-SO_3M \quad (1),$$

wherein
  $Rf^1$ is a perfluoroalkyl group comprising 1 to 6 carbon atoms,
  p, q, and r are independently an integer of 1 to 6,
  M is a cationic atom or atomic group,
  n is 0 or 1, and
  R is hydrogen atom, an alkyl group comprising 1 to 12 carbon atoms, or a group of formula (2):

$$Rf^2-C_sH_{2s}-CH(OH)-C_tH_{2t}- \quad (2),$$

wherein
  $Rf^2$ is a perfluoroalkyl group comprising 1 to 6 carbon atoms, and
  s and t are independently an integer of 1 to 6.

2. The compound of claim 1, wherein n is 0.

3. The compound of claim 1, wherein $Rf^1$ is a perfluoroalkyl group comprising 6 carbon atoms.

4. The compound of claim 1, wherein R is a group of formula (2).

5. The compound of claim 4, wherein $Rf^2$ is a perfluoroalkyl group comprising 6 carbon atoms.

6. The compound of claim 1, wherein $Rf^1$ is a straight chain perfluoroalkyl group comprising 6 carbon atoms.

7. The compound of claim 1, wherein p and q are 1, and r is 1 or 2.

8. The compound of claim 1, wherein M is an alkaline metal selected from the group consisting of Na, K, and Li.

9. The compound of claim 2, wherein $Rf^1$ is a perfluoroalkyl group comprising 6 carbon atoms.

10. The compound of claim 2, wherein R is a group of formula (2).

11. The compound of claim 10, wherein $Rf^2$ is a perfluoroalkyl group comprising 6 carbon atoms.

12. The compound of claim 2, wherein $Rf^1$ is a straight chain perfluoroalkyl group comprising 6 carbon atoms.

13. A surfactant, comprising the fluorine-comprising compound of claim 1.

14. A surfactant composition, comprising:
  the surfactant of claim 13; and
  an aqueous medium.

15. An aqueous resin emulsion, comprising the surfactant of claim 13.

16. A floor polish composition, comprising the surfactant of claim 13.

17. A surfactant, comprising the fluorine-comprising compound of claim 2.

18. A surfactant composition, comprising:
  the surfactant of claim 17; and
  an aqueous medium.

19. An aqueous resin emulsion, comprising the surfactant of claim 17.

20. A floor polish composition, comprising the surfactant of claim 17.

* * * * *